(12) United States Patent
Saied

(10) Patent No.: US 7,083,596 B2
(45) Date of Patent: Aug. 1, 2006

(54) ANESTHETIZER WITH AUTOMATIC NEEDLE DECOMMISSIONING MECHANISM

(75) Inventor: V. C. Saied, 2802 Hamilton Blvd., Wichita Falls, TX (US) 76038

(73) Assignee: V. C. Saied, Wichita Falls, TX (US)

( * ) Notice: Subject to any disclaimer, the term of this patent is extended or adjusted under 35 U.S.C. 154(b) by 362 days.

(21) Appl. No.: 10/177,266

(22) Filed: Jun. 19, 2002

(65) Prior Publication Data
US 2003/0014019 A1 Jan. 16, 2003

Related U.S. Application Data (60) Provisional application No. 60/299,628, filed on Jun. 20, 2001.

(51) Int. Cl.
A61M 5/00 (2006.01)

(52) U.S. Cl. ........................ 604/110; 604/187

(58) Field of Classification Search ................. 604/91, 604/92, 191, 199, 82–87, 89, 90, 110, 181, 604/187, 220, 240
See application file for complete search history.

(56) References Cited

U.S. PATENT DOCUMENTS

| | | | |
|---|---|---|---|
| 2,617,359 A * | 11/1952 | Van Horn | .............. 102/512 |
| 4,887,998 A * | 12/1989 | Martin et al. | .............. 604/110 |
| 4,968,168 A | 11/1990 | Chern | |
| 4,976,561 A | 12/1990 | Kageyama | |
| 5,048,990 A | 9/1991 | Hashimoto et al. | |
| 5,190,521 A | 3/1993 | Hubbard et al. | |
| 5,279,583 A | 1/1994 | Shober, Jr. et al. | |
| 5,279,586 A | 1/1994 | Balkwill | |
| 5,360,410 A * | 11/1994 | Wacks | .............. 604/232 |
| 5,385,551 A | 1/1995 | Shaw | |
| 5,389,076 A | 2/1995 | Shaw | |
| 5,411,492 A | 5/1995 | Sturman et al. | |
| 5,423,758 A | 6/1995 | Shaw | |
| 5,505,694 A | 4/1996 | Hubbard et al. | |
| 5,578,011 A | 11/1996 | Shaw | |
| 5,593,391 A | 1/1997 | Stanners | |
| 5,632,733 A | 5/1997 | Shaw | |
| 5,634,909 A | 6/1997 | Schmitz | |
| 5,674,204 A | 10/1997 | Chanoch | |
| 5,688,251 A | 11/1997 | Chanoch | |
| 5,913,629 A | 6/1999 | Hazzard | |
| 5,921,966 A | 7/1999 | Bendek et al. | |
| 5,957,896 A | 9/1999 | Bendek et al. | |
| 5,964,735 A | 10/1999 | Alexander | |
| 5,984,900 A | 11/1999 | Mikkelsen | |
| 6,004,297 A | 12/1999 | Steenfeldt-Jensen et al. | |
| 6,050,735 A | 4/2000 | Hazzard | |
| 6,312,412 B1 | 11/2001 | Saied et al. | |
| 6,322,540 B1 | 11/2001 | Grabis et al. | |
| 6,383,167 B1 | 5/2002 | Kirchhofer et al. | |

* cited by examiner

Primary Examiner—Kevin C. Simmons
(74) Attorney, Agent, or Firm—Haynes and Boone, LLP (57) ABSTRACT

A medical device includes a hollow needle having a distal end and a proximal end, and a substantially flexible storage chamber for storing a medical preparation. The storage chamber is disposed spaced apart from the proximal end of the needle. The medical device further includes a needle shield, a mechanism operable to advance the storage chamber toward the proximal end of the needle and enabling fluid communication thereof with the medical preparation in the storage chamber, and a mechanism operable to decommission the needle substantially immediately using the needle shield after injecting the medical preparation with the needle.

25 Claims, 8 Drawing Sheets

ANESTHETIZER WITH AUTOMATIC NEEDLE DECOMMISSIONING MECHANISM

RELATED APPLICATION

This patent application claims the benefit of Provisional Patent Application, Application No. 60/299,628, entitled Anesthetizer with Needle Retraction or Covering Mechanism, filed on Jun. 20, 2001.

TECHNICAL FIELD OF THE INVENTION

The present invention relates generally to the field of medical products, and more particularly to a device such as an anesthetizer with automatic needle decommissioning mechanism.

BACKGROUND OF THE INVENTION

The insertion of a large gauge needle or an intravenous (I.V.) catheter can be a frightening and painful experience. The sight alone of the large gauge needle is enough to cause a patient to become anxious and tense. The patient's reaction causes his muscles to become tense and hard, making needle penetration difficult and painful.

Typically, the I.V. needle must be inserted into a vein along the forearm or on the back of a hand. It is not uncommon for a first attempt to insert the I.V. needle to fail because it is difficult to locate a vein in some patients. As a result, further painful probing is often required to find the vein and insert the needle. After insertion, an I.V. catheter may remain in place for an extended period of time. The site of penetration may remain painful due to the pulling and stretching of the catheter. As a result, the patient may be subject to pain and suffering repeatedly and needlessly. It is therefore in the best interest of the patients and medical and health professionals that the patient's pain and fear associated with I.V. needle and other large gauge needles are addressed.

An additional concern for today's medical and health professionals and staff is the possibility of contracting infectious blood-borne diseases through accidental contact with used needles. Measures, guidelines and legislation for the safe handling and disposal of used needles and syringes have been prescribed. Some needle retraction and shield mechanisms have been heretofore proposed to remove the needle point from possible exposure and contact with personnel after use. However, these devices often require the user to affirmatively actuate or initiate the mechanism to retract or shield the needle, which renders the device ineffective in some instances where the user is either careless, forgetful, or in a rush such as in emergency situations, for example. Other proposed devices require a two-handed operation to retract or cover the needle, which makes these devices inconvenient to use in many instances.

SUMMARY OF THE INVENTION

There is an urgent desire to provide medical and healthcare professionals and staff syringes and other devices with a needle that is automatically decommissioned after use to prevent accidental needle pricks. The present invention provides a device such as an anesthetizer that has an automatic needle retraction or covering mechanism to decommission the needle. It should be noted that the automatic mechanisms described herein are equally applicable to syringes and other devices in which it is desirable to render a sharp edge or point inaccessible.

In an embodiment of the present invention, a medical device includes a hollow needle having a distal end and a proximal end, a substantially flexible storage chamber for storing a medical preparation, the storage chamber being disposed spaced apart from the proximal end of the needle. The medical device further includes a needle shield, means operable to advance the storage chamber toward the proximal end of the needle and enabling fluid communication thereof with the medical preparation in the storage chamber, and means operable to decommission the needle substantially immediately using the needle shield after injecting the medical preparation with the needle.

In another embodiment of the present invention, an anesthetizer includes a substantially flexible storage chamber for containing a numbing solution, a fine gauge hollow needle having a distal end and a proximal end, the needle operable to conduct the numbing solution from its proximal end to its distal end, a needle shield, and a decommissioning device operable to decommission the needle using the needle shield substantially immediately after injecting the numbing solution into a patient's skin with the needle, the numbing solution operable to raise a skin wheal.

In yet another embodiment of the present invention, a medical device includes a substantially flexible storage chamber for containing a solution, a hollow needle having a distal end and a proximal end, the proximal end of the needle operable to pierce the storage chamber and the needle operable to conduct the solution from its proximal end to its distal end, means for shielding the needle, and means for actuating the needle shielding means substantially immediately after injecting the solution into a patient's skin with the needle, the solution operable to raise a skin wheal.

BRIEF DESCRIPTION OF THE DRAWINGS

For a more complete understanding of the present invention, the objects and advantages thereof, reference is now made to the following descriptions taken in connection with the accompanying drawings in which.

DETAILED DESCRIPTION OF THE DRAWINGS

The preferred embodiment of the present invention and its advantages are best understood by referring to FIGS. 1 through 6 of the drawings, like numerals being used for like and corresponding parts of the various drawings.

It should be noted that although the present invention is primarily described as operating in an anesthetizer used to numb a site intended for a later needle insertion, the present invention is equally applicable and operable for use with a syringe and other such devices to decommission the needle so that it can no longer pose a threat to personnel. The present invention is especially suitable for disposable devices but can be implemented in non-disposable devices as well.

FIGS. 1A through 1E are elevational and cross-sectional views of an embodiment of an anesthetizer 10 with automatic needle retraction mechanism according to the teachings of the present invention. Anesthetizer 10 includes a body 12 and a cap 14 protecting the opening at a distal end thereof. Anesthetizer 10 further includes an opening 16 in body 12 that permits user access to a storage bulb or reservoir 18 containing one or more solutions primarily used to numb an injection site. Storage bulb 18 has pliable and flexible walls that can be squeezed together by a user to decrease its interior volume to eject solutions stored therein. In an embodiment, storage bulb may have two or more compartments containing medicated preparations that are mixed and intermingled when the walls between the compartments are breached by force exerted by the user to eject the solutions. A removable spacer 20 is used to maintain a predetermined distance between an actuation button 22 located at a proximal end of anesthetizer 10 and body 12, so that storage bulb 18 remains spaced apart from needle 24 housed within body 12. Needle 24 is preferably a fine gauge needle, such as 23 gauge or less, that does not elicit very noticeable pain when inserted shallowly. Needle 24 is held in a holder 23, which helps to position and orient the needle. A biasing member or spring 26 is disposed about needle 24 against needle holder 23. Biasing member 26 may be a helical spring or a spring of any suitable shape or construction. Biasing member 26 may be hereinafter referred to as being in communication contact with the needle—there may not necessarily be direct contact therebetween, but the forces exerted by the biasing member is used to urge the needle. A retractable nose cone 28 is disposed at a distal end of anesthetizer 10 and shields the tip of needle 24.

Referring more specifically to FIGS. 1B through 1E for more detailed views of anesthetizer 10, nose cone 28 is coupled to or in contact with a collar 34 with a plurality of circumferential and spaced elongated protruding ridges 35 that operate to engage and interface with a plurality of elongated channels 25 formed on an interior surface of the distal end of body 12. Channels 25 include elongated grooves oriented along the same axis as needle 24. Ridges 35 further have regularly-shaped protruding edges that correspond and cooperate with regularly-shaped protruding ridges or teeth 33 of a ratchet 32. For example as shown, ridges 33 may have a trapezoidal shape that correspond with the angular configuration of the end of channels 25. Ratchet 32 is also coupled to collar 34 so that the respective ridges stay in contact with one another. Needle holder 23 and needle 24 are held stationary relative to anesthetizer body 12 while ratchet 32 and collar 34 are operable to displace and extend nose cone 28 out from the distal end of anesthetizer 10, and retract nose cone 28 therefrom and thus exposing needle 24 for use. Channels 25 further define a stop configuration 25b that includes a bottom 25c of the channel and an angular notch 25d. Channel stops 25b are defined in alternate channels.

In operation, the user removes cap 14 and spacer 20 and exerts pressure on actuation button 22 to close the gap previously occupied by spacer 20. The advancement of actuation button 22 in effect pushes storage bulb 18 toward the proximal tip of needle 24, which pierces its wall and makes contact with medicated solution(s) therein. The user then positions the distal end of anesthetizer 10 over the intended injection site and lowers anesthetizer 10 and its nose cone 28 onto the injection site and presses down thereon. The downward pressure pushes nose cone 28 into body 12 against biasing element 26. The downward pressure also forces the ridges 33 of ratchet 32 to be displaced beyond channels 25. Ratchet 32 rotates due to the shape of ridges 33 of ratchet 32 and the shape of ridges 35 of collar 34. In other words, it is easier for ratchet 32 to rotate in one direction versus the other because of the trapezoidal shape of its teeth 33. After rotation for a predetermined amount determined by the width of ridges 33 and spacing therebetween, ridges 33 of ratchet 32 and collar 34 come to rest on "top" of channels 25, being urged against channels 25 by spring 26. With ratchet 32 and collar 34 resting against channels 25, a space is created between collar 34 and nose cone 28. Nose cone 38 is thus able to retract when anesthetizer 10 is lowered onto the patient's skin, where the needle tip and a predetermined length thereof extend beyond nose cone 38 and into the patient's tissues. The user at this time may squeeze or otherwise exert pressure on storage bulb 18 to force the numbing solution or fluid therein to go through needle 24 and enter into the patient's tissues at the injection site. In a preferred embodiment such as described in U.S. Pat. Nos. 5,505,694 and 5,190,521 issued to Hubbard et al. on Apr. 9, 1996 and Mar. 2, 1993, respectively, anesthetizer 50 may be used to inject an anesthetizing solution to raise a skin wheal in preparation for the subsequent insertion of a larger gauge needle. As a result, a skin wheal is raised at the injection site that operates to numb the patient's skin and underlying tissues so that the insertion of a larger gauge needle does not cause unnecessary pain for the patient.

As the user completes the injection of the numbing solution, he exerts downward pressure again to force nose cone 38 slightly further up into body 12, which causes ratchet 32 to be displaced beyond channels 25 and to rotate again relative thereto. This time, ridges 33 of ratchet 32 are able to fall in between channels 23, thus eliminating the space between collar 34 and nose cone 28, and extending nose cone 28 out from body 12. The user may perform these functions in one continuous action that can become second nature. The stops, embodied as notch 25d and bend 25c formed in channels 25 or a similar structure may be used to prevent nose cone from re-retracting into body 12 or prevent ratchet 32 from further rotation after the first use. It may be seen that the retraction mechanism described above operates much like a retractable ballpoint pen. Variations on this mechanism now known or later developed are equally applicable to the present invention. The user may replace cap 14 onto the distal end of anesthetizer 10 and discard it into an approved container.

FIGS. 2A through 2D are cross-sectional views of another embodiment of an anesthetizer 50 with automatic needle retraction mechanism according to the teachings of the present invention. Anesthetizer 50 includes a body 52 that encloses a storage chamber or reservoir 54 for holding a liquid, such as medicated solutions, anesthetizing solutions, etc. Storage bulb 54 is constructed of a substantially pliable and flexible material. Storage bulb 54 is coupled to a substantially rigid plunger member 55 that is in turn coupled to a knob 56 at a proximal end of anesthetizer 50 that is used to assert downward pressure (see FIG. 2E) to compress a plurality of accordion folds 57 and advance storage bulb 54 toward a hollow needle 60. Needle 60 is preferably a fine gauge needle, such as 23 gauge or less. Knob 56 is preferably constructed of a substantially rigid material. Plunger member 55 is preferably rigid and solid up to accordion folds 57. Plunger member 55 further includes an external thread that meets and matches a first internal thread on an interior surface of body 52, as referenced by numeral 58. Needle 60 is securely held by a bulb seat 62 so that a first tip of needle 60 is substantially aligned with storage bulb 54. Bulb seat 62 also includes a threaded fitting 68 with external thread that meets and matches with a second internal thread 70 on an inner surface of body 52. Preferably threaded fitting 68 uses 50/50 threads or another configuration that facilitates easy coupling. Further coupled to bulb seat 62 is a biasing mechanism such as one or two resilient springs 64. The biasing mechanism 64 may affix to the distal end of the body 52, which may also operate to shield the needle 60 when not in use. A separate needle shield 66 may be provided, which may shield the needle 60 instead of, or in addition to, the distal end of the body 52. Additionally, the biasing mechanism 64 may affix to the needle shield 66 instead of, or in addition to, the distal end of the body 52. The biasing mechanism 64 may be a helical spring or a spring of any suitable shape or construction. A cap 72 to protect the distal end of needle 60 from contamination before use is secured over the needle opening in the distal end of anesthetizer 50.

Figures 1A, 1B:
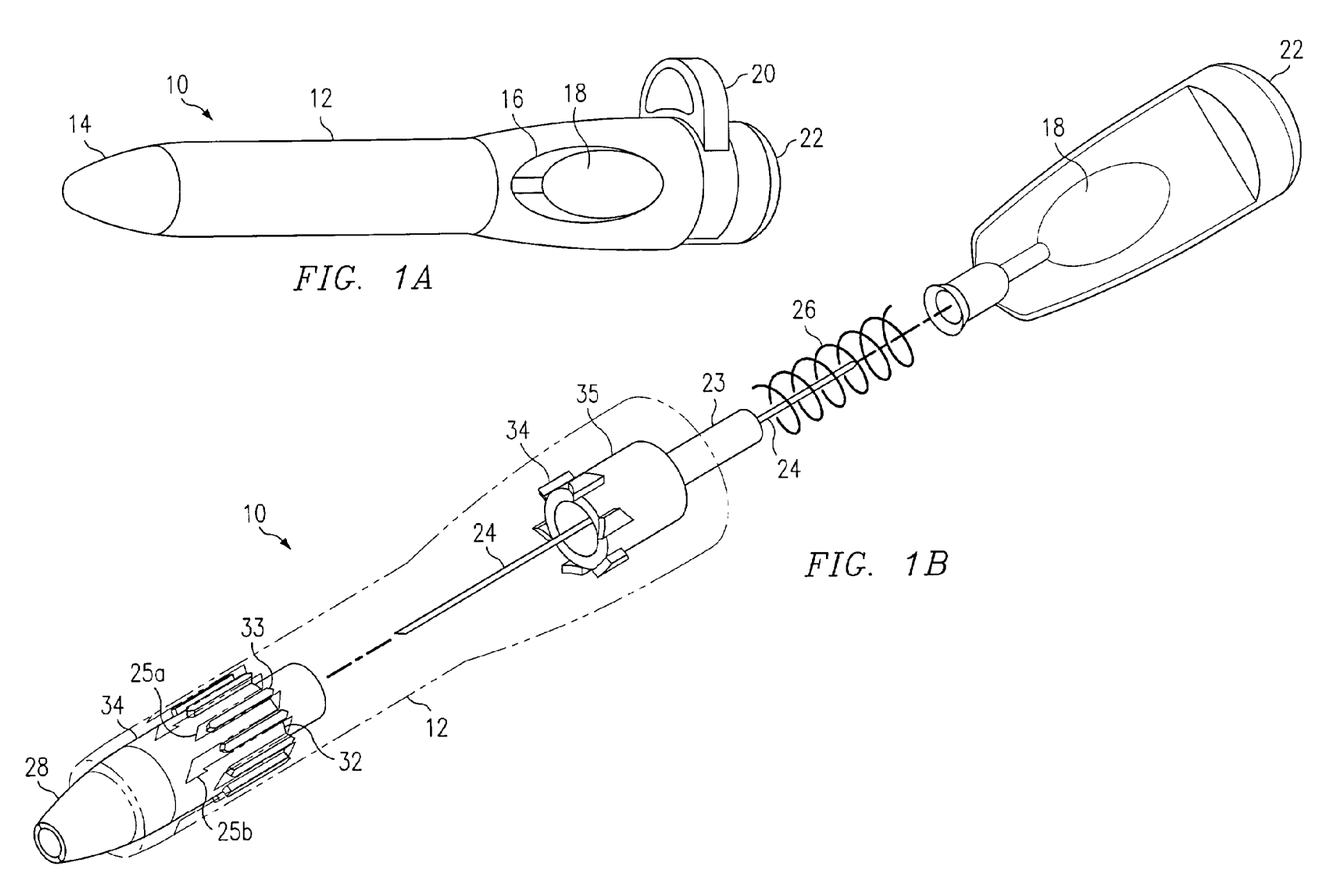
FIGS. 1A through 1E are elevational and cross-sectional views of an embodiment of an anesthetizer with automatic needle retraction mechanism according to the teachings of the present invention.
Figure 1C:
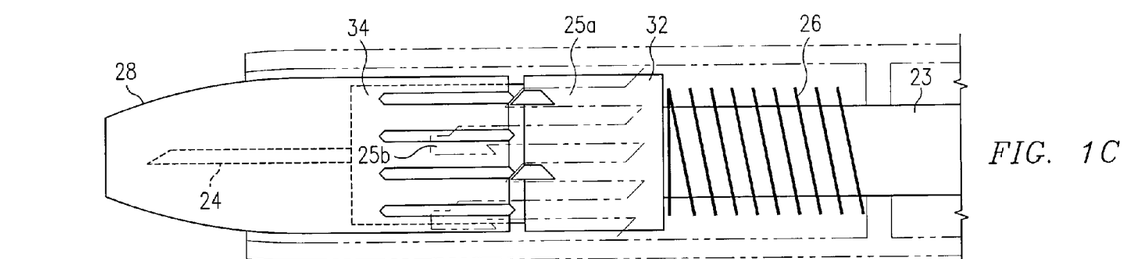
Figure 1D:
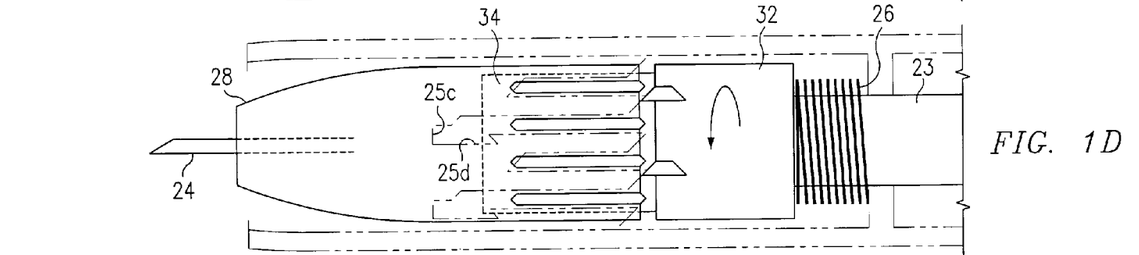
Figure 1E:
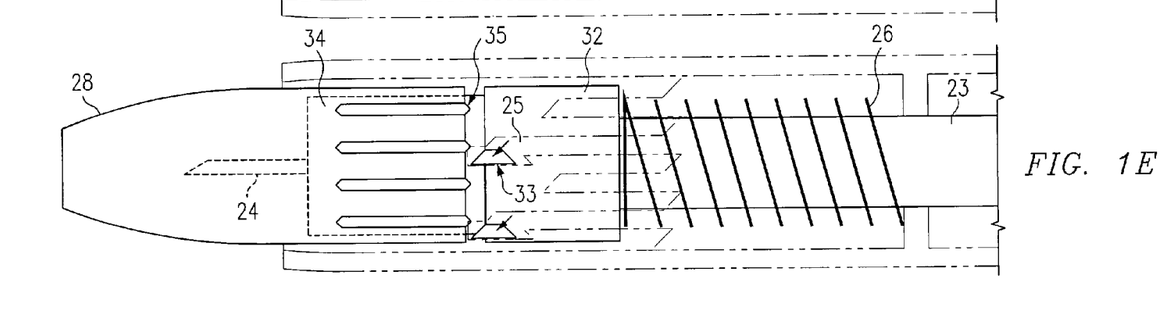
Figure 2A:
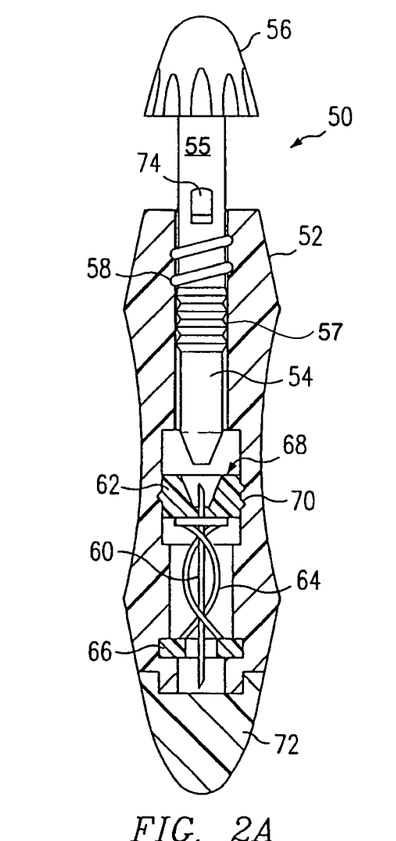
FIGS. 2A through 2D are cross-sectional views of another embodiment of an anesthetizer with automatic needle retraction mechanism according to the teachings of the present invention
Figure 2B:
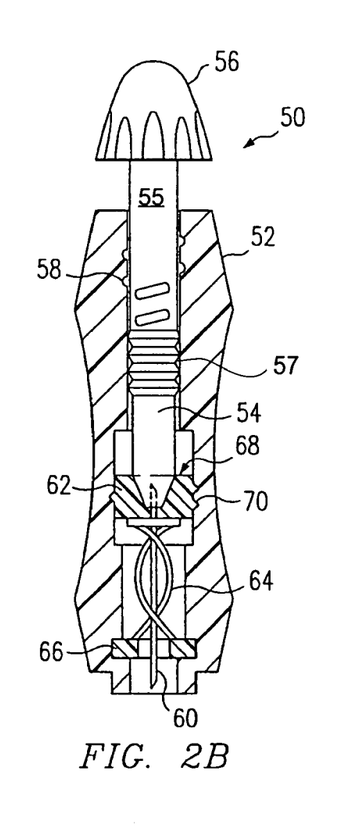
Figure 2C:
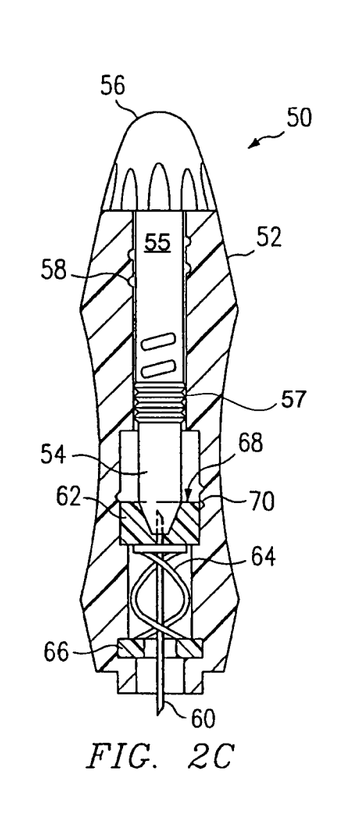

Referring now to FIGS. 2A through 2E, a preferred operating process of anesthetizer 50 is described below. A user first rotates knob 56 an amount determined by first thread 58 to advance plunger member 55 further into anesthetizer body 52 and causing the distal end of storage bulb 54 to move into bulb seat 62 and be pierced by needle 60, as seen in FIG. 2B. At this point, needle 60 is in fluid communication with the solution contained inside storage bulb 54. As the user continues to turn knob 56, threaded fitting 68 advances beyond second internal thread 70, as seen in FIG. 2C. In order to assist the user to rotate knob 56 for the predetermined amount, colored markings and/or indentations may be made on knob 56 and the proximal end of body 52 to allow the user to continue the rotation until the markings are in alignment, for example.

Figure 2D:
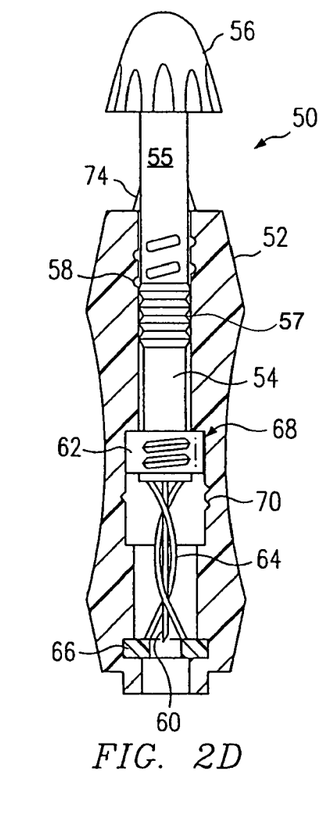
Figure 2E:
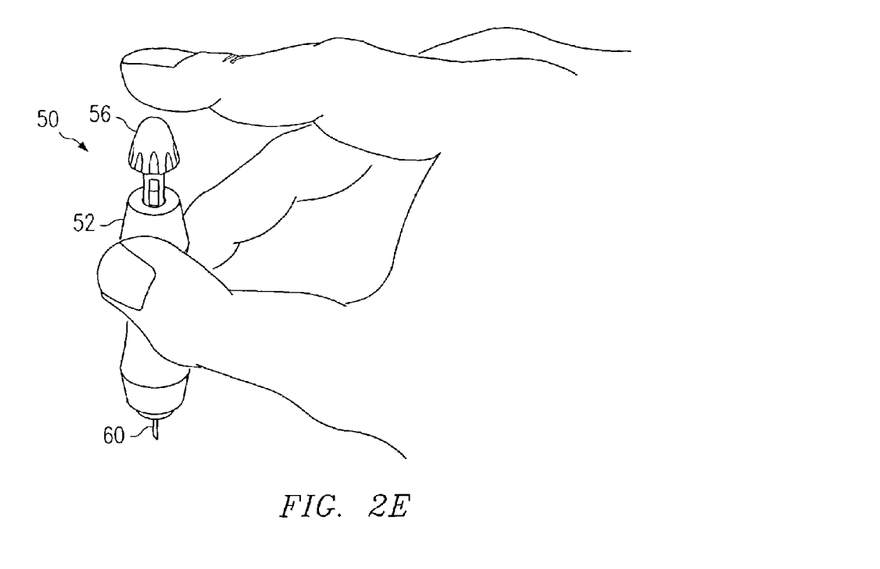
FIG. 2E is an illustration showing a preferred manner in which the anesthetizer shown in FIGS. 2A through 2D is held and used.

Thereafter, the user may then remove cap 72 and hold anesthetizer 50 in the manner shown in FIG. 2E for injection. Anesthetizer 50 is shown held substantially perpendicular relative to the injection surface, but the angle at which anesthetizer 50 is held may vary depending on the preference of the user, the type of injection, the type of medicated solution to be injected, the gauge and length of needle 60, etc. The user then exerts pressure on knob 56, which compresses accordion folds 57 and decreases the internal volume of storage bulb 54. Continued downward pressure of knob 56 and plunger member 55 causes biasing members 64 to be compressed and bulb seat 62 to advance toward distal opening of anesthetizer 50. The tip of needle 60 thus protrudes out from the distal opening and beyond the distal tip of anesthetizer 50, as shown in FIG. 2C. In this embodiment, only a very short length of needle 60 needs to be exposed to inject an anesthetizing solution into the patient's skin. In a preferred embodiment such as described in U.S. Pat. Nos. 5,505,694 and 5,190,521, anesthetizer 50 may be used to inject an anesthetizing solution to raise a skin wheal in preparation for the subsequent insertion of a larger gauge needle. After a sufficient amount of medicated solutions have been injected into the patient's skin, the user releases knob 56 and allows plunger member 55, knob 56 and bulb seat 62 to be biased and urged toward the proximal end of anesthetizer by springs 64 and accordion folds 57. Thus the springs 64 and/or the accordion folds 57 may operate to automatically decommission the needle 60 by retracting the needle 60 back into the distal end of the body 52 and/or retracting the needle 60 to a position behind the needle shield 66. As shown in FIG. 2D, bulb seat 62 is biased past second internal threads 70 and pushed far into anesthetizer body 55 so that the needle point is no longer exposed. One or more downward protruding locking tabs 74 coupled to the exterior surface of plunger 55, once extended beyond the proximal opening of body 52, prevents plunger member 55 from moving back into anesthetizer body 52. Therefore, locking tabs 74 prevents the needle point from being exposed again after use. It may be seen that anesthetizer 50 is operable to automatically retract and lock the needle point without requiring the user to activate the mechanism or requiring two-handed operation. The means operable to advance the storage chamber towards the proximal end of the needle includes knob (56) and internal threads (58). The means operable to decommission the needle includes the biasing mechanism (64) and the locking tab (74).

Figure 3:
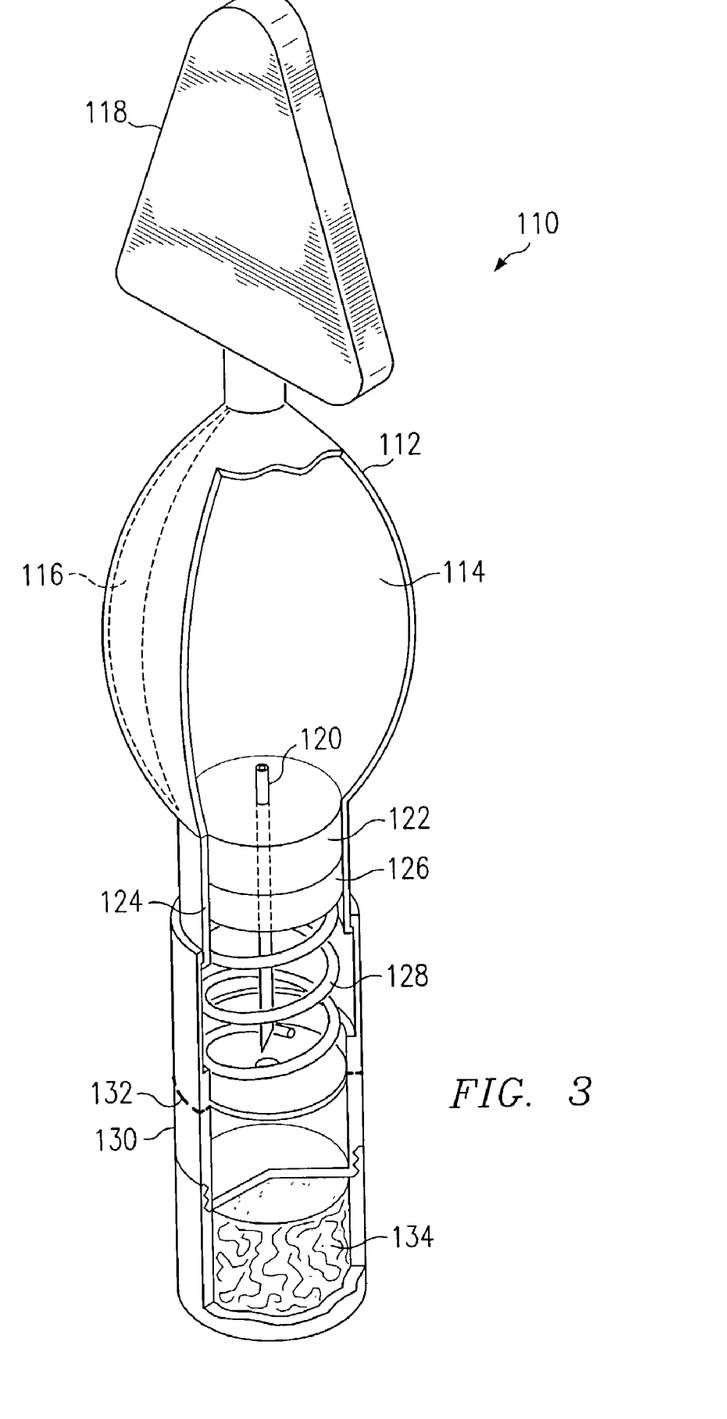
FIG. 3 is a cross-sectional view of another embodiment of an anesthetizer with automatic needle retraction mechanism according to the teachings of the present invention.

FIG. 3 is a cross-sectional view of another embodiment of an anesthetizer 110 with automatic needle retraction mechanism according to the teachings of the present invention. Anesthetizer 110 includes a substantially flexible and pliable vial, ampule or storage bulb or reservoir 112 that may contain one or more separated chambers 114 and 116 to store one or more solutions. The chamber walls between the separate chambers are constructed such that finger pressure on storage bulb 112 is sufficient to breach the walls and allow the solutions to mix, interact and react. Storage bulb 112 may be coupled to an optional handle 118 at its proximal end operable to provide ease of handling to the users. A fine gauge needle 120 is held securely by a bulb seat 122 coupled to a neck of storage bulb 112. A LUER-LOK (registered trademark of Becton, Dickinson & Company, Rutherford, N.J.)—type coupling 24 may be coupled to bulb seat 122 and biased by biasing members 126. LUER-LOK coupling 124 includes threading 128 and a movable and generally cylindrical needle housing or covering 129. A cap 130 having a score mark 132 covers the needle at the distal end of anesthetizer 110. An optional antiseptic applicator 134 laden with ethyl alcohol, iodoform, betadine or another suitable preparation is further disposed on the end of cap 130 or proximal end of the anesthetizer, for example. Antiseptic applicator 134 may be a sponge, cotton swab, or some other suitable material. Antiseptic applicator 134 may be shielded from the environment by a covering, lid or foil shield (not explicitly shown) that may be removed prior to use. The concept of the antiseptic applicator is applicable to all embodiments shown and contemplated herein.

Anesthetizer 110 may be constructed of a commercially available plastic vial or ampule filled with the desired medicated solution(s). Anesthetizer 110 may be packaged and distributed already assembled as shown or it may be assembled by the user immediately prior to use. For example, the user may connect a filled plastic vial or ampule containing the solution(s) (storage bulb 112) with a needle assembly using coupling 124. As the user rotates the needle assembly with respect to storage bulb 112, the needle pierces the wall of the storage chamber and comes in contact with the solution(s) contained therein. Thereafter, the user may remove a covering of antiseptic applicator and use it to prepare the injection site. In the embodiment shown, cap 130 may be removed from anesthetizer 110 by applying pressure and snapping off the cap along scored mark 132. The user then positions anesthetizer 110 over the injection site perhaps with the bottom surface of movable needle housing 129 gently in contact with the injection site skin surface. The user may then squeeze storage bulb 112 and further press downward into the skin surface. The downward pressure pushes up cylindrical needle housing 129 to its compressed or retracted position and exposes the tip and a length of the needle. At the same time, the medicated solutions are forced out of storage bulb 112 and flow into the patient's tissues to preferably raise a skin wheal or otherwise numb the injection site. The downward pressure also compresses biasing members 126, which upon release of the downward pressure by the user after injection, causes needle housing 129 to be biased to its extended position. When needle housing 129 is returned to its extended position, the needle point is contained within the housing. If preferred, a locking mechanism such as locking tabs shown in FIG. 2D or other suitable means may be used to keep needle housing 129 in the extended position after use.

Figure 4A:
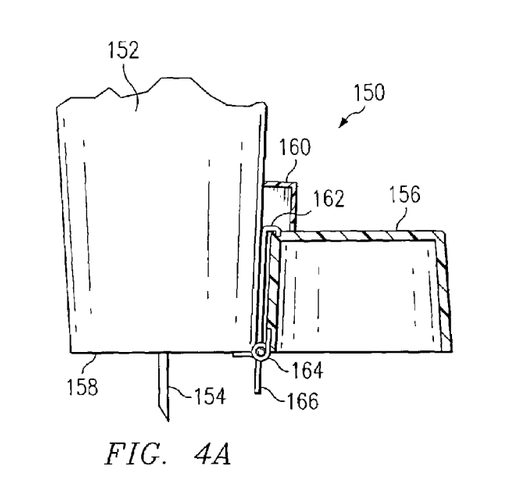
FIGS. 4A and 4B are partial cross-sectional views of an embodiment of an anesthetizer with automatic needle covering mechanism according to the teachings of the present invention.

FIG. 4A is a partial cross-sectional view of an embodiment of an anesthetizer 150 with automatic needle covering mechanism according to the teachings of the present invention. Anesthetizer 150 comprises a body 152 housing a hollow needle 54 and medicated solution(s) to be injected using needle 54. Needle 54 is securely affixed in a position such that its point extends a predetermined distance beyond the body of anesthetizer 150. Anesthetizer 150 includes a cap 156 operable to automatically enclose and cover the needle point and distal end 158 of anesthetizer 150 after use. Cap 156 further includes a mechanism housing 160 that houses a catch 162 that holds a biasing spring hinge 164 of cap 156 operable to displace cap 156 from its inactivated position as shown in FIG. 4A to its activated position covering the needle shown in FIG. 4B. The displacement of cap 156 by biasing spring 164 is put in motion by an actuator 166.

Figure 4B:
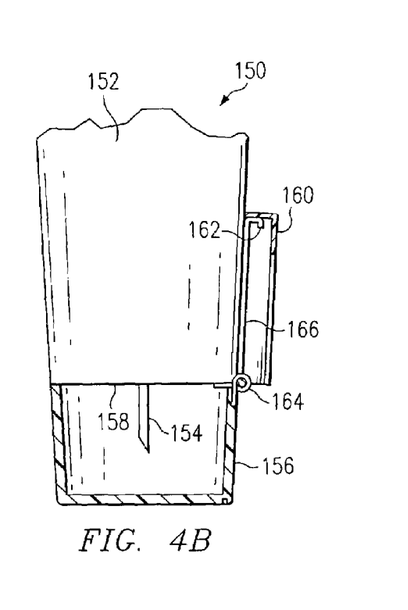
Figures 5A, 5D:
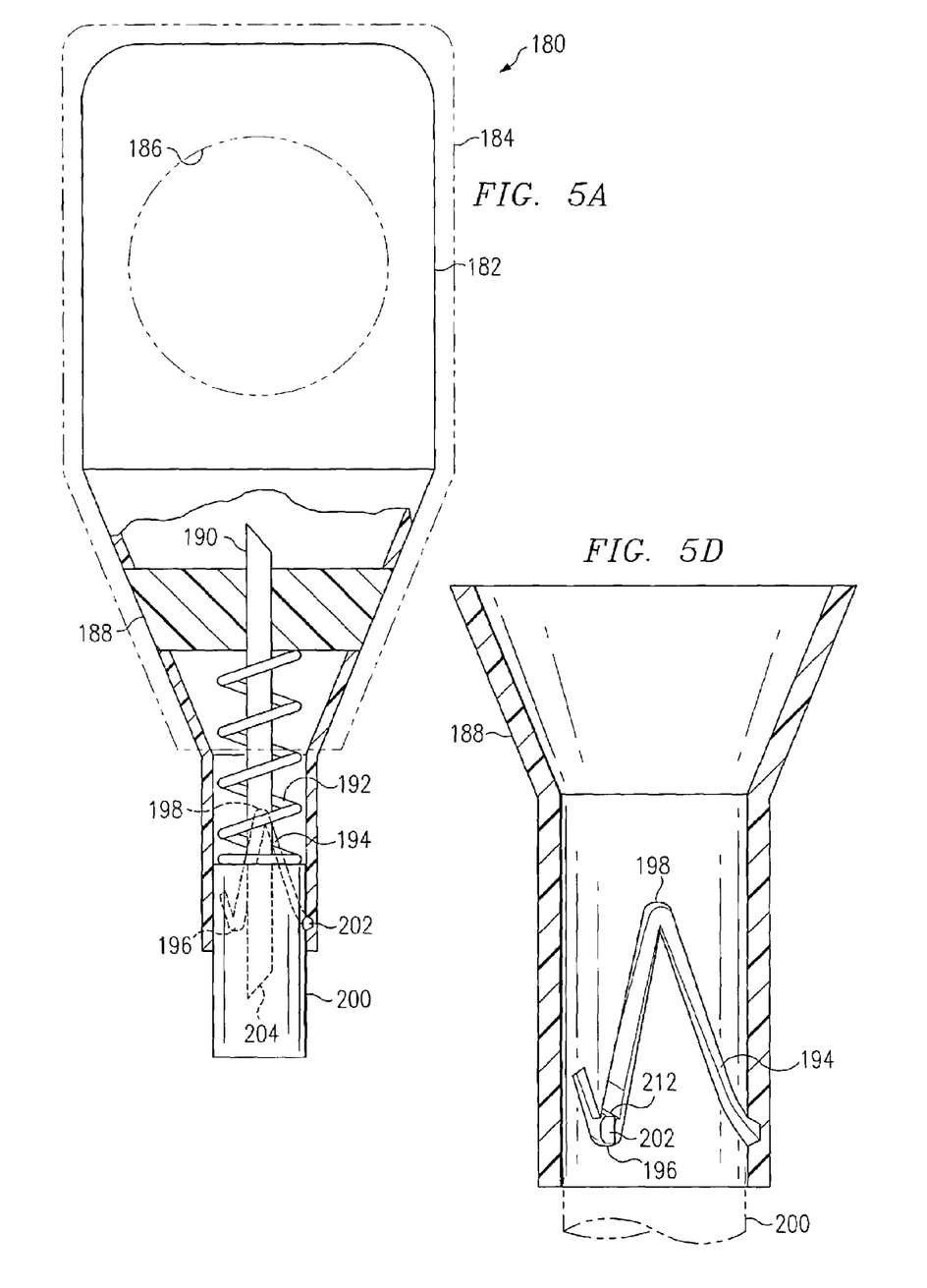
FIGS. 5A through 5D are cross-sectional views of yet another embodiment of an anesthetizer with automatic needle retraction mechanism according to the teachings of the present invention.
Figure 5B:
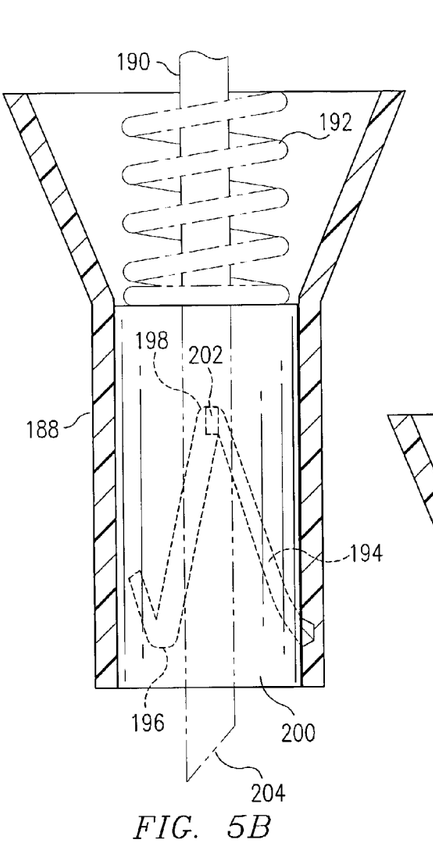
Figure 5C:
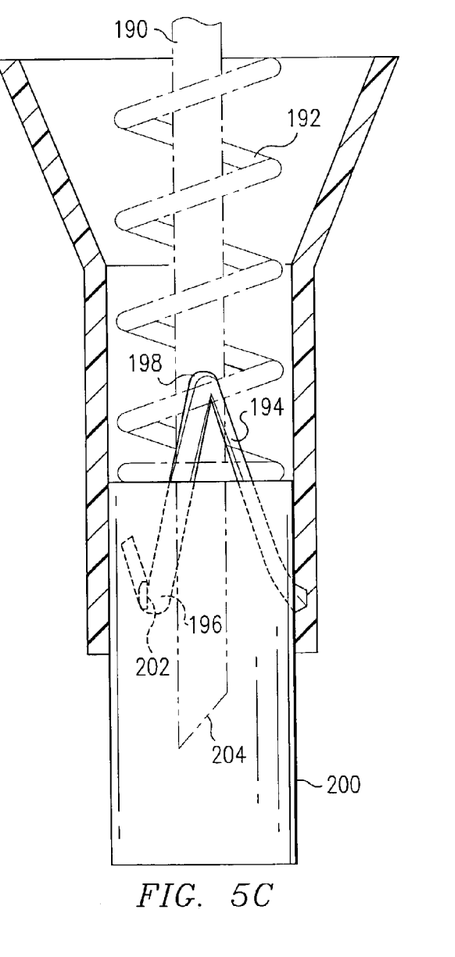

In operation, as the user lowers anesthetizer 150 at the injection site, and pushes needle 154 into a patient's skin 168 to make the injection, actuator 166 is pushed upward and causes catch 162 to release cap 156. Alternatively, actuator 166 may cause catch 162 to release biasing spring hinge 164. Upon actuation, biasing spring hinge 164 causes cap 156 to flip downward about a pivot point at spring hinge 164. Cap 156 may then temporarily rest against the patient's skin near the injection site. However, as the user moves anesthetizer 150 away from the patient's skin, spring hinge 164 further biases cap 156 to its activated position covering needle 154, as shown in FIG. 4B.

It may be seen that the size and structure of housing 160 is determined by the mechanism it houses and may be eliminated altogether. For example, if catch 162 can be incorporated with spring hinge 164, then housing 160 may not be necessary. Furthermore, the structure of actuator 166 may be determined upon the material used and how much pressure is needed to release catch 162. Anesthetizer 150 is designed to be actuated automatically without requiring the user to perform any extra step in his/her typical procedure. The implementation shown in FIGS. 4A and 4B are exemplary and modifications and adjustments thereof may be made to effect the same.

FIGS. 5A through 5D are cross-sectional views of yet another embodiment of an anesthetizer 180 with automatic needle retraction mechanism according to the teachings of the present invention. Anesthetizer includes a storage bulb 182 containing one or more medicated solutions. An optional housing 184 with an opening 186 may be provided to enclose storage bulb 182. Storage bulb 182 and/or housing 184 is coupled to a bulb seat 188 that houses a needle retraction mechanism according to the teachings of the present invention. A fine gauge hollow needle 190 is securely held in housing bulb seat 188. A needle covering housing or tube 200 is biased by a biasing element 192. Further, a tab or finger 202 located on an exterior surface of needle covering tube 200 is disposed in a groove 194 formed in an interior surface of bulb seat 188 and having a predetermined configuration, examples of which are shown in FIGS. 5A through 5D. Finger 202 is operable to travel in groove 194 as tube 200 is displaced longitudinally in bulb seat 188. Groove 194 includes a bend 196 or a one-way tab or valve 212 (FIG. 5D) near one end thereof, which functions as a stop to prevent tube 200 from retracting and exposing the needle after the needle has been used.

In operation, anesthetizer 180 can be operated easily with one hand. The user squeezes storage bulb 182 slowly to prime needle 190 so that it is in fluid communication with the solution(s) stored in the storage bulb. The user then lowers anesthetizer 180 onto the injection site with needle covering tube 200 lightly touching the skin surface. The user then exerts pressure downward, which forces needle covering tube 200 to retract into bulb seat 188. Needle point 204 is thus exposed by the retracting tube 200 and used to deliver the solution(s) to the patient's tissues at the intended injection site as the user squeezes storage bulb 182. As needle covering tube 200 retracts, its finger 202 travels along groove 194 from its first end to its peak 198, at which point tube 200 is fully retracted and exposing the maximum length of needle 190. Thereafter, as user lifts up anesthetizer 180 from the injection site, tube 200 is biased by biasing element 192 to force it back downward along with moving finger 202 further along groove 194 toward bend 196 near its second end. When tube 200 descends fully and completely shields needle point 204, finger 202 also reaches bend 196. When any future pressure is exerted on tube 200, bend 196 causes finger 202 to remain at the second end of groove 194 and thus preventing tube 200 from retracting again. In the embodiment shown in FIG. 5D, one-way valve or tab 212 presents an obstacle to finger 200 so that it is not capable of traveling back toward peak 198 in the groove.

Figure 6A:
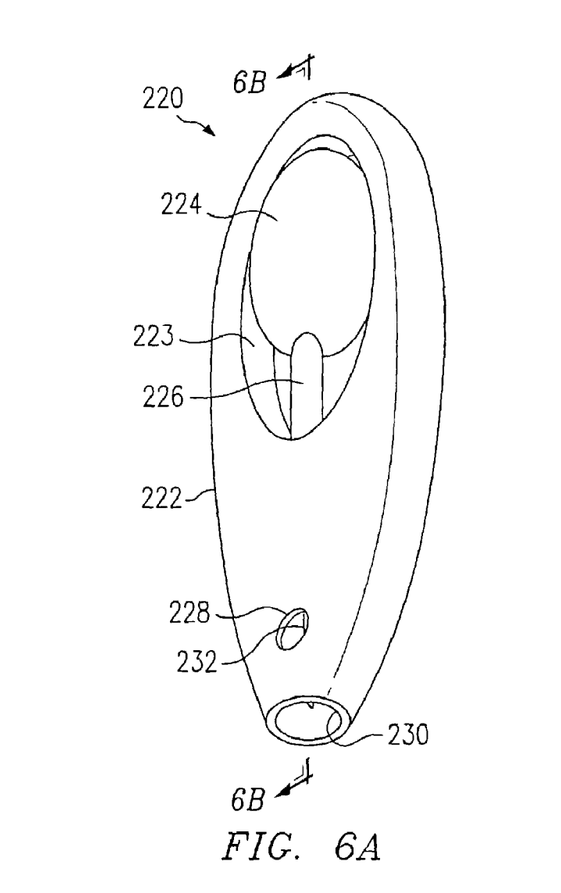
FIGS. 6A through 6C are elevational and cross-sectional views of yet another embodiment of an anesthetizer with automatic needle retraction mechanism according to the teachings of the present invention.
Figure 6B:
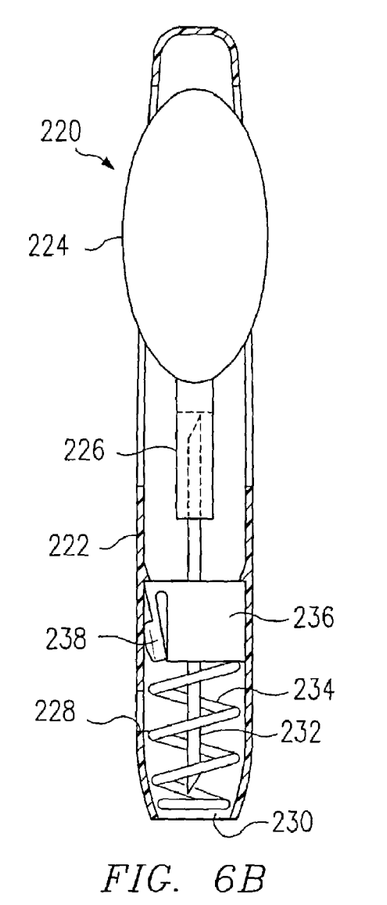
Figure 6C:
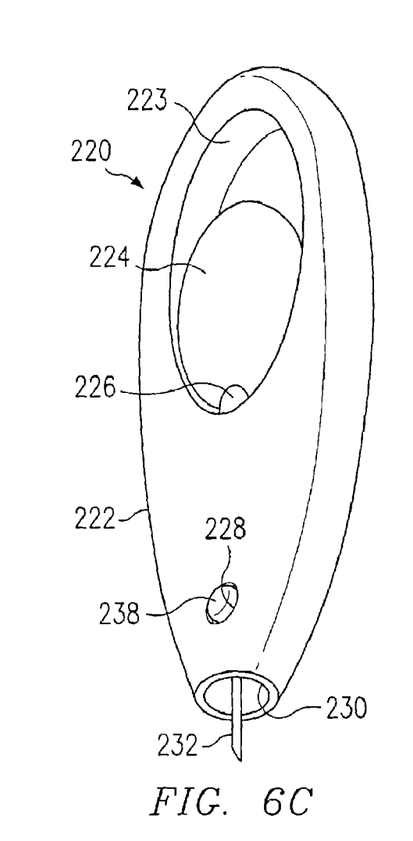

FIGS. 6A through 6C are elevational and cross-sectional views of yet another embodiment of an anesthetizer 220 with automatic needle retraction mechanism according to the teachings of the present invention. Anesthetizer 220 includes a body 222 with a first opening 223 that exposes a portion of a substantially pliable and flexible storage chamber or storage bulb 224 that contains a medical preparation or solution. Anesthetizer body 222 may include a second opening identical to first opening 223 on an opposed side of body 222. Storage bulb 224 may include a liquid passageway 226. A needle 232 is securely held by a needle seat or holder 236. Needle holder 235 is gently urged by a biasing element 234 toward the proximal end of anesthetizer 220, so that needle 232 is in its retracted position. The biasing member may be a helical spring or a spring of any suitable shape or construction. Anesthetizer body 222 includes a small opening 228 that is operable to receive a button 238 that is biased outwardly. Button 238 comes into alignment with small opening 228 when needle 232 is in its extended position, which is actuated by the user pushing or sliding storage bulb 224 toward needle 232. Button 238 is operable to pop into small opening 228 to temporarily lock needle 232 in its extended position while anesthetizer 220 is being used.

In operation, the user may gently rest the distal tip of anesthetizer 220 on a patient's skin at the intended injection site. The user may hold the anesthetizer perpendicularly with respect to the skin surface or at an angle. The user then pushes storage bulb 224 toward needle 232 and enables the medicated solution in storage bulb 224 to be in fluid communication with needle 232, and further pushes needle seat 236 against biasing member 234 and extends needle 232 out of distal opening 230 to its extended position. When needle 232 reaches its extended position, button 238 snaps into small opening 228 and counters the force of biasing member 234 to continually maintain the extended position of needle 232. The user then injects the medicated solution into the patient's tissues by squeezing the storage bulb. Immediately thereafter, the user gently pushes in button 238 to allow the force generated by biasing element 234 to retract needle 232 into the anesthetizer body. It may be seen that the user may easily accomplish decommissioning the needle using just one hand, while freeing the other hand to perform other functions Although the various embodiments of the present invention are shown separately, it should be understood that structural elements of different embodiments may be combined without departing from the spirit of the invention. For example, the embodiments shown in FIGS. 3 and 5A–5D, although shown with the needle already piercing the wall of the storage chamber, may be implemented with the storage chamber initially spaced apart from the needle. Different locking mechanisms may also be used on different embodiments of the present invention shown in the figures.

The various embodiments of the medical device of the present invention provide an easy and substantially automatic way to retract or cover the needle point so that it would not present a health hazard to medical and health care professionals and staff. The operations of the anesthetizer can be actuated without using two hands to free up the other hand for other important activities. The needle point is deactivated or decommissioned automatically upon the completion of the injection or with slight or minor actuation using the same hand. The anesthetizer is primarily used to substantially numb an area of the patient's skin in preparation for the insertion of a larger gauge needle, such as an IV catheter. This eases the patient's mind and fear and thus makes the entire process more comfortable and easy for the patient as well as the healthcare professional. The present invention is also applicable to other medical devices such as syringes, scalpels that have a needle or sharp edge that may become contaminated with blood-borne infectious agents during use.

What is claimed is:

1. A medical device, comprising:
   a hollow needle having a distal end and a proximal end;
   a substantially flexible storage chamber for storing a medical preparation, the storage chamber having at least two separate chambers operable to contain at least two separate solutions, the at least two separate chambers being divided by a wall that breaks when a force is applied to the storage chamber to allow the at least two solutions to mingle, the storage chamber being disposed spaced apart from the proximal end of the needle;
   a needle shield;
   means operable to advance the storage chamber toward the proximal end of the needle and enabling fluid communication thereof with the medical preparation in the storage chamber; and
   means operable to decommission the needle substantially immediately using the needle shield after injecting the medical preparation with the needle.

2. The medical device, as set forth in claim 1, further comprising a body having a distal end and a proximal end and housing the needle, the body defining an opening providing user access to the storage chamber.

3. The medical device, as set forth in claim 2, wherein the needle shield comprises a distal portion of the body.

4. The medical device, as set forth in claim 3, wherein the automatic needle decommissioning means comprises: a biasing member in communication contact with the needle and urging the needle toward the proximal end of the body and retracting the distal end of the needle inside the body; and a locking member preventing the needle distal end from advancing beyond the distal end of the body after injecting the medical preparation with the needle.

5. The medical device, as set forth in claim 4, wherein the locking member comprises a locking tab.

6. The medical device, as set forth in claim 4, further comprising an actuator operable to release the needle to enable the biasing member to bias the needle toward the proximal end of the body.

7. The medical device, as set forth in claim 2, wherein the needle shield comprises a needle housing operable to retract into the distal end of the body.

8. The medical device, as set forth in claim 7, wherein the automatic needle decommissioning means comprises: the needle housing operable to be displaced between an extended position covering the distal end of the needle and a retracted position exposing the distal end of the needle; and a biasing member in communication contact with the needle housing and biasing the needle housing toward the extended position.

9. The medical device, as set forth in claim 8, further comprising a locking device preventing the needle housing from moving into its retracted position after injecting the medical preparation with the needle.

10. The medical device, as set forth in claim 9, wherein the needle housing comprises: a substantially cylindrical tube encircling the needle; a tab formed on an exterior surface of the tube; a groove having a predetermined configuration formed on an interior surface of the medical device body, the tab operable to be slidably engaged within the groove; and the locking device including a bend in the groove operable to prevent the tab from traveling in an direction to displace the needle housing to its retracted position.

11. The medical device, as set forth in claim 10, wherein the locking device further comprises a one-way tab operable to prevent the tab from traveling in the direction to displace the needle housing to its retracted position.

12. The medical device, as set forth in claim 2, wherein the needle shield comprises a cap coupled to the body and operable to cover the distal end of the body.

13. The medical device, as set forth in claim 12, wherein the automatic needle decommissioning means comprises: the needle cap operable to be displaced between an extended position covering the distal end of the body and a retracted position exposing the distal end of the body; a biasing member in communication contact with the needle cap and operable to bias the needle cap toward the extended position;

and an actuator operable to automatically release the needle cap in response to completing injection of the medical preparation.

14. The medical device, as set forth in claim 13, wherein the actuator comprises a pin coupled to the biasing member and operable to contact with a patient's tissues when the injection is being made, the pin contact triggering the biasing member to be released and moving the needle cap to its extended position.

15. The medical device, as set forth in claim 1, further comprising an antiseptic applicator.

16. The medical device, as set forth in claim 1, wherein the needle shield comprises a distal portion of a body housing the hollow needle.

17. The medical device, as set forth in claim 16, wherein the automatic needle decommissioning means comprises:
 a biasing member in communication contact with the needle and urging the needle toward the proximal end of the body and retracting the distal end of the needle inside the body; and
 a locking member preventing the needle distal end from advancing beyond the distal end of the body after injecting the medical preparation with the needle.

18. The medical device, as set forth in claim 17, wherein the locking member comprises a locking tab.

19. The medical device, as set forth in claim 18, further comprising an actuator operable to release the needle to enable the biasing member to bias the needle toward the proximal end of the body.

20. An anesthetizer, comprising:
 a body having a distal end and a proximal end;
 a substantially flexible storage chamber for containing a numbing solution;
 a fine gauge hollow needle having a distal end and a proximal end housed within the body, the needle operable to conduct the numbing solution from its proximal end to its distal end while the substantially flexible storage chamber is depressed to decrease its internal volume;
 a needle shield;
 a decommissioning device operable to decommission the needle using the needle shield substantially immediately after injecting the numbing solution into a patient's skin with the needle, the numbing solution operable to raise a skin wheal;
 a locking member preventing the needle distal end from advancing beyond the distal end of the body after injecting the medical preparation with the needle; and
 an antiseptic applicator.

21. The anesthetizer, as set forth in claim 20, wherein the storage chamber further comprises at least two separate chambers operable to contain at least two separate solutions, the at least two separate chambers being divided by a wall that is breakable when a force is applied to the storage chamber to allow the at least two separate solutions to mingle.

22. The anesthetizer, as set forth in claim 20, wherein the needle shield comprises a cap coupled to the body and operable to cover the distal end of the body.

23. The anesthetizer, as set forth in claim 20, wherein the automatic needle decommissioning device comprises:
 a biasing member in communication contact with the needle and urging the needle toward the proximal end of the body and retracting the distal end of the needle inside the body; and
 a locking member preventing the needle distal end from advancing beyond the distal end of the body after injecting the medical preparation with the needle.

24. The anesthetizer, as set forth in claim 23, wherein the locking member comprises a locking tab.

25. The anesthetizer, as set forth in claim 23, further comprising an actuator operable to release the needle to enable the biasing member to bias the needle toward the proximal end of the body.

* * * * *